United States Patent [19]

Schneider et al.

[11] Patent Number: 4,804,479
[45] Date of Patent: Feb. 14, 1989

[54] PROCESS FOR DETOXIFYING A BOTTOMS DRAW-OFF FROM A HIGH TEMPERATURE CHLORINATION REACTOR

[75] Inventors: Wolfgang W. Schneider, Broadview Heights, Ohio; William A. Wagner, Houston, Tex.

[73] Assignee: The B. F. Goodrich Company, Akron, Ohio

[21] Appl. No.: 171,995

[22] Filed: Mar. 23, 1988

[51] Int. Cl.$^4$ ............................................... C02F 1/74
[52] U.S. Cl. ................................. 210/754; 210/763; 210/806; 210/912; 570/262
[58] Field of Search .................. 210/712, 718, 722, 737, 210/750, 754, 758, 708, 761–763, 805, 806, 909, 912; 570/262; 203/31, 34, 53

[56] References Cited

U.S. PATENT DOCUMENTS

| | | | |
|---|---|---|---|
| 3,115,528 | 12/1963 | Benner, Jr. et al. | 570/262 X |
| 4,307,261 | 12/1981 | Beard, Jr. et al. | 570/262 |
| 4,412,086 | 10/1983 | Beard, Jr. et al. | 570/262 |
| 4,415,460 | 11/1983 | Suciu et al. | 210/754 |
| 4,533,473 | 8/1985 | Burks, Jr. et al. | 210/754 |
| 4,543,190 | 9/1985 | Modell | 210/761 X |
| 4,614,643 | 9/1986 | Doane | 423/140 |
| 4,758,352 | 7/1988 | Feldner et al. | 210/758 X |

FOREIGN PATENT DOCUMENTS 41-13606 7/1966 Japan .
1380497 1/1975 United Kingdom .

Primary Examiner—Tom Wyse
Attorney, Agent, or Firm—Alfred D. Lobo; Nestor W. Shust; Joe A. Powell

[57] ABSTRACT

Under certain operating conditions, an emulsion of an acidified unfiltrable tarry bottoms stream from a reactor for the chlorination of ethylene to 1,2-dichloroethane can be demulsified and separated in a phase separation tank. The presence of FeCl$_3$ in an amount more than 5 ppm Fe in the separated organic waste, fouls the reboiler and lower internals of a "heavies" column in which the separated organic waste is concentrated, and deactivates the catalyst in a Catoxid fluid bed reactor in which the concentrate is burned. By maintaining an iron salt chlorination catalyst in a concentration which results in 2000 ppm to 4000 ppm of Fe in the HTC reactor bottoms, and operating the HTC reactor at a temperature in the range from about 90° C. to 120° C. and a pressure in the range from 9 psig to 12 psig, an unfiltrable reactor bottoms drawoff is produced which may be acidified without forming an emulsion. Formation of an emulsion is avoided by mixing each volume of the HTC bottoms drawoff with at least 50 volumes of dilute aqueous HCl in a concentration range from 2 to 4% so as to demulsify the emulsion into aqueous acid and organic phases. The mixture is gravity-separated in a phase separation tank by decantation. The lower layer (60–70% by wt EDC, the remainder being heavies) is concentrated by recovering EDC overhead and producing a bottoms concentrate in which the Fe is present in no more than 50 ppm. The concentrate may be economically disposed of in a Catoxid reactor using a support-free gamma alumina catalyst found to be highly sensitive to iron.

4 Claims, 1 Drawing Sheet

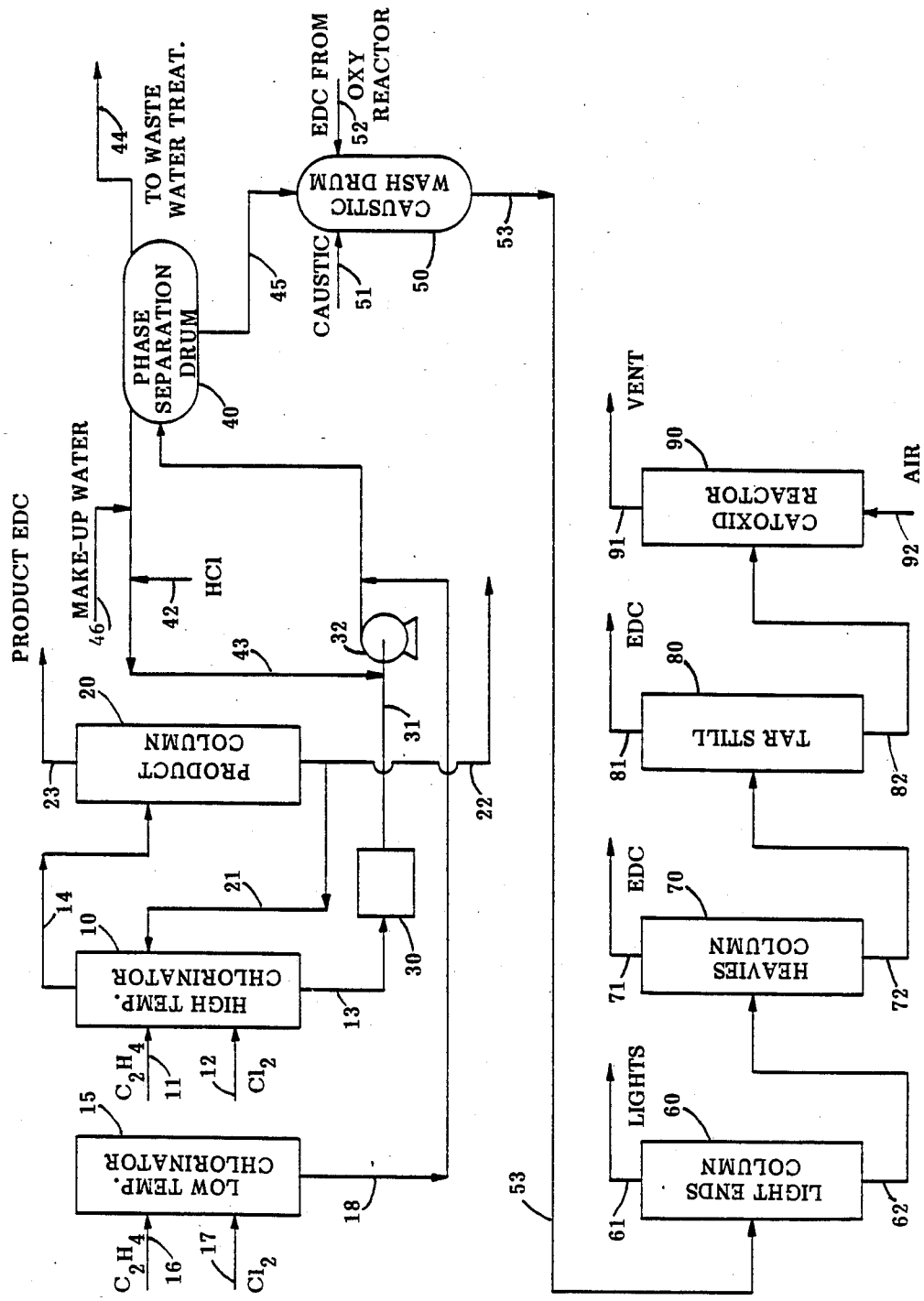

PROCESS FOR DETOXIFYING A BOTTOMS DRAW-OFF FROM A HIGH TEMPERATURE CHLORINATION REACTOR

BACKGROUND OF THE INVENTION

This invention relates to breaking an emulsion formed when a predominantly 1,2-dichloroethane (ethylene dichloride, "EDC") stream containing at least 15% by weight (wt) of highboiling chlorinated hydrocarbons (also referred to as highboils, or "CHC" for brevity), and contaminated with iron salts, is acidified with aqueous hydrochloric acid. If the emulsion is not broken, the aqueous and organic phases cannot be separated by gravity, allowing the mixture of phases to settle. Since other methods of phase separation of such a mixture are not economical, the ability to break the emulsion and make the separation is critical in a commercially viable process. This invention is directed to demulsifying an acidified bottoms draw-off from a high temperature chlorination (HTC) reactor, which draw-off is predominantly EDC containing about 2000 ppm to about 4000 ppm of Fe present as a salt, and at least 15% by wt highboils, then separating the aqueous and organic phases. The organic phase contains less than 10 ppm Fe which is concentrated in an organic waste stream to be incinerated by contact with a fluid-bed catalyst without poisoning it. The catalyst is held in a catalytic oxidation ("Catoxid") reactor in a commercial plant for the production of more than 600 million pounds per year of vinyl chloride.

The "direct chlorination of ethylene" is the basis for the widely used commercial catalytic process for the production of EDC. The reaction is controlled by mass transfer, with absorption of ethylene as the limiting factor whether the reaction is carried out with a slight excess of ethylene, or as an alternative option, a slight excess of chlorine, fed to the reactor. The heat of reaction is dissipated either through conventional water cooling of a typical low temperature chlorination ("LTC") also referred to as a "non-boiling" reactor because it operates in the range from about 50° C. to about 65° C.; or, by operating the reactor at, or near, the boiling point of EDC under superatmospheric pressure up to about 25 psig, preferably from about 5 psig to 25 psig, hence referred to as a HTC reactor, also referred to as a "boiling reactor" when it is operated at the boiling point of EDC.

The direct chlorination reaction may be written:

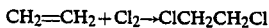

$$CH_2=CH_2 + Cl_2 \rightarrow ClCH_2CH_2Cl$$

and theoretically, neither water nor HCl is formed as a product of this reaction. In practice, in the presence of oxygen, some water may be formed in some side reactions, and some HCl is formed in another side reaction which may be written:

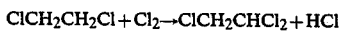

$$ClCH_2CH_2Cl + Cl_2 \rightarrow ClCH_2CHCl_2 + HCl$$

The precise amount of HCl formed depends upon the type of catalyst used in the HTC reactor, upon the liquid medium in which the reaction is carried out (typically a chlorinated hydrocarbon such as EDC), and upon the conditions of reaction.

The direct chlorination reaction is carried out with a variety of iron-containing catalysts such as ferric chloride, sodium or potassium tetrachloroferrate, and ammonium tetrachloroferrate which must be maintained in a specified concentration in the reaction mass. During the reaction, numerous chlorinated byproducts are formed which must be removed to avoid stifling the efficient formation of the desired EDC. Of course, it would be best if the byproducts could be removed without removing the catalyst, but since this is not possible, the catalyst is depleted when the byproducts are purged from the reactor.

The draw-off is predominantly EDC, which may be present in the range from about 50% to about 98% by wt of the liquid reaction medium in the HTC reactor, typically from 60 to 95% by wt, the remainder being "heavies". By "heavies" we refer to polychlorinated CHC which are higher boiling than EDC. These heavies include polymeric materials some of which are solid or semi-solid. Economics dictate that the EDC in the draw-off be recovered in a distillation column for the heavies ("heavies column"). The problem is that the presence of $FeCl_3$ in the bottoms of the heavies column results in agglomerates which are caked onto the internals of the column, the surfaces of the tubes in the column's reboiler, the valves, etc., requiring frequent shutdowns to clean the equipment.

Further, if the draw-off from the bottom of the heavies column ("heavies" draw-off) is to be disposed of by combustion in a catalytic oxidation reactor using a catalyst which is progressively deactivated by the presence of metals, particularly iron, sodium, potassium and the like, the metals content of the feed to the oxidation reactor must be decreased to a level at which the deactivation of the oxidation catalyst is tolerable.

This invention relates particularly to the use of such salts as the tetrachloroferrates and $FeCl_3$ which must be removed from the bottoms draw-off of the HTC reactor if the draw-off is to be concentrated, and the concentrate oxidized in a specific type of catalytic oxidation reactor, namely the "Catoxid" reactor. The Catoxid reactor uses a gamma alumina catalyst which is deactivated by contact with metals such as iron, sodium and potassium even when they are present in minimal concentration. The heavies draw-off is typically neutralized with ammonium hydroxide or ammonia before being fed to the Catoxid reactor. When the neutralized and concentrated draw-off contains more than 50 ppm Fe present as $FeCl_3$ or a ferrate salt, the catalyst is deactivated in an unacceptably short period of time. Thus more than 50 ppm Fe in a wastestream fed to the Catoxid reactor is said to be toxic to the oxidation catalyst, and the catalyst is said to be adversely sensitive to the presence of metals, because it is uneconomical to replenish the deactivated catalyst.

The iron concentration (computed as ppm of Fe) in the bottoms draw-off is tied to the concentration of $FeCl_3$ after acidification of the draw-off, because it has been found that, when the operation of the heavies column and/or tar still, the HTC reactor, and the Catoxid reactor are combined under carefully regulated conditions, a concentration of from 2000 ppm to 4000 ppm Fe (which may be present as $FeCl_3$ or a tetrachloroferrate salt) in the HTC bottoms draw-off essentially eliminates its emulsification provided (1) the draw-off is contacted with an aqueous hydrochloric acid having a concentration of from 2% to 4% by wt; (2) the draw-off is mixed with at least a fifty-fold excess of the aqueous HCl acid over the amount of HTC bottoms draw-off; and, (3) only the draw-off from a LTC reactor, if one is operated in the plant, and no other chlorocarbon stream containing Fe contaminants, may be added to acidified HTC bottoms before it is demulsified and separated into aqueous and organic phases.

It will be evident that the concentration of catalyst in the HTC reactor must be replenished so as to result in a concentration of from 2000 ppm to about 4000 ppm Fe in the bottoms draw-off stream from the HTC reactor before it is acidified with aqueous hydrochloric acid. It is equally evident that, since the goal of the detoxification process is to provide a draw-off from the heavies column and/or a tar still with less than 50 ppm Fe, and the waste heavies from the HTC reactor eventually finds its way to the heavies column, it would seem desirable to minimize the concentration of Fe in the HTC bottoms, not deliberately run it in the 2000-4000 ppm range.

The rate of withdrawal of the bottoms draw-off from the HTC reactor is such as to control the build-up (concentration) of heavy, high-boiling chlorinated byproducts in the HTC reactor. EDC in the HTC bottoms draw-off must be recovered in the overhead of the heavies column, and the remaining heavies bottoms further stripped of EDC and desirable CHC, then disposed off by incineration in a fluid bed oxidation reactor. The particular make-up of the bottoms draw-off with particular respect to the emulsionforming CHC solids and polymers, depends upon the concentration of chlorination catalyst used in the HTC reactor and its process operating conditions.

In the particular commercial process of interest herein, the bottoms draw-off contains in excess of 60%, preferably about 80%, by weight EDC, and also about 15% by wt of higher-boiling (than EDC) liquid CHC byproducts ("highboils") including a semi-solid mass of polychlorinated CHC and other unidentified relatively high molecular weight compounds collectively referred to as "tar" because it is an unfiltrable muck. By "unfiltrable" is meant that it can be filtered through a basket filter having a coarse mesh size larger than about 0.0625 inch (1.59 mm), say about 12 mesh U.S. Standard), but it is impractical to filter the tar through a smaller mesh size than 177 microns (80 mesh) on a commercial scale, even if such filtration removed the emulsifiers in the stream, which, once the emulsion is formed, by definition, filtration cannot. Filtration of the HTC bottoms stream is impractical even after the addition of a filter aid, because the filter is blinded in less than an hour. Filtration through a 105 micron filter (140 mesh) blinds the screen almost immediately even when the organic stream is diluted with 10 volumes of dilute HCl acid.

It is this HCl acid-diluted tarry two-phase emulsion of EDC, heavies and aqueous ferric chloride, which is to be separated into aqueous and organic phases by a simple decantation step. Formation of an emulsion does not permit separation of the aqueous and organic phases by decantation because a supernatant aqueous layer is not formed. For such separation, when an emulsion is formed, the emulsion must be broken or the phases will not separate in a phase separation drum.

The aqueous phase is led to waste water treatment. The separated organic phase (hereafter "separated waste organic stream" because it is phase separated) is neutralized with alkali, usually caustic soda, ammonia or ammonium hydroxide, to convert the ferric chloride to ferric hydroxide, and the neutralized separated waste stream is led to a light ends column. The bottoms from the light ends column is led to a heavies column, then preferably to a tar still, for recovery of the EDC.

If the Fe concentration in the bottoms draw-off of the HTC reactor is sufficiently high to be of concern, the obvious solution to the problem is to acidify the draw-off stream with dilute HCl, but this causes such severe emulsification that the emulsion cannot be broken using prior art techniques on a commercial scale, and the organic and aqueous phases cannot be separated by settling. It is this critical problem of how to demulsify the acidified CHC, and make the separation of aqueous acid and organic phases, which has never been addressed in the prior art with sufficient detail as to provide the essential critical teachings to enable one skilled in the art to solve the problem. This deficiency is particularly conspicuous because it is well recognized that the behavior of different emulsion systems is highly specific, so that it is unrealistic to expect that a system can be demulsified without specific teachings as to how this should be done.

We are aware of some general tenets of methods for demulsifying a stream, including (a) flocculating the stream to such an extent that coalescence of the droplets is no longer prevented by the interfacial film, (b) removing the emulsifying agent from the interface, and (c) forming an emulsion of the opposite type. We are also aware of the many ways to accomplish the foregoing methods, including special mechanical treatments, heat treatments, electrical deposition, freezing, exposure to supersonic vibrations, filtration through a filter medium which is preferentially wetted by the discontinuous phase of the emulsion, and addition of surface active agents or other special chemicals. We have been unable to break the emulsion we form with prior art processes, try though we may, and we know of no one who has done so if only on a bench scale in a laboratory.

Such a prior art process is disclosed in U.S. Pat. No. 4,533,473 to Burks, Jr. et al, assigned to Stauffer Chemical Company which discloses the same basic problems with the separation of $FeCl_3$, and the same process operations as in our plant for the production of EDC, except for the difference in how the waste CHC streams are treated. In the '473 process, several waste CHC streams are combined and concentrated in a tar still or by vacuum distillation to produce a residual product ("residue") of highboils, as was conventionally done, and still is, in the prior art. This residue includes EDC, 1,1-dichloroethane, dichloroethylenes, trichloroethylene, perchloroethylene, pentachloroethylene, 1,1,2-trichloroethane (triane), chloroform, 1,1,1-trichloroethane (methylchloroform), 1,1,2,2-tetrachloroethane; penta- and hexachloroethanes, and chlorobutadienes such as chloroprene. Most of all, combining waste streams produces a combination of emulsifiers which produce so stable an acidified aqueous emulsion that, despite affirmations and allegations to the contrary, a combination of several waste CHC streams cannot be demulsified, then separated in a phase separation drum.

The '473 process failed to recognize that the emulsification effect of emulsifiers from the heavies CHC stream from the HTC bottoms in particular, was so intense that the emulsion formed upon acidification defied separation except under narrowly defined conditions, particularly that the concentration of dilute HCl acid for demulsification was critical, and that the amount of dilute acid required for doing so was orders of magnitude greater than what was estimated to be sufficient. The problem of dealing with the emulsion formed with the HTC bottoms containing ferric salts, was simply overlooked, as evidenced by the statement "depending upon the nature of the waste stream and the metallic contaminant, an emulsion may be formed which may easily be broken." (see col 4, lines 40–43). This oversight is re-affirmed in the statement "Even should an emulsion form, it has been found that treatment according to this invention creates emulsions which may readily be broken by passing the treated material through a filter and coalescer, optionally with the addition of a filter aid or by centrifugation (sic)." (see col 5, lines 24–28).

The '473 patent particularly sets out to teach how to detoxify any CHC stream, before or after concentration, or, any one or more of combined waste streams from (i) a HTC reactor in a process for making EDC, and (ii) other processes for the production of chlorinated hydrocarbons such as chlorinated benzenes and various chloromethanes, described and schematically illustrated in FIGS. 1–4 of the reference. The process, schematically illustrated in FIG. 5, teaches first filtering the waste residue(s) from one or more of the foregoing chlorination processes to remove particulate solids, then contacting the filtrate of the residue with a dilute aqueous solution of a mineral acid, then coalescing, filtering or centrifuging the acidified residue "if necessary, to break any emulsion which may have formed" (see col 9, lines 44–45). Not only is there little weight accorded the seriousness of the emulsification problem, but a broad range of aqueous acid is said to be effective. It is stated that the dilute aqueous solution contains preferably from 2 to about 10 percent by wt of acid, the volume ratio of dilute acid to organic material in the waste stream being at least 1:1 to dissolve the $FeCl_3$ in the residue.

If the emulsion had been successfully demulsified, it would have been evident that breaking the emulsion to make the separation was the overriding consideration to enable one to carry out the process. The economic desirability of combining several waste heavies CHC streams for Fe removal would have been unequivocally negated by the exigent requirements for breaking the emulsion.

Our attempts to remove slightly higher than 50 ppm Fe concentration by acidification with aqueous HCl were unsuccessful because of the formation of the emulsion which defied partition into the aqueous and organic phases economically. It was therefore quite surprising that a much higher concentration, namely 2000–4000 ppm of Fe in HTC bottoms, appears to generate emulsifiers which form an emulsion amenable to being demulsified, and is the key to a successful separation.

We find that, either before or after we acidify a draw-off which contains 2000–4000 ppm Fe, the draw-off cannot be filtered through a screen smaller than 80 mesh (U.S. Standard). We find that any attempt to filter out small solids such as may initiate formation of the emulsion, leads to blinding the filter. We have found no compound to coalesce the emulsion, and no adsorbent to adsorb the contaminants in any practical fashion. The sole purpose of a basket filter is to remove large lumps of solids and heavy, creamy semi-solid agglomerates referred to as "rags" (because of their appearance), to minimize fouling of the equipment.

The operating difficulty of dealing with the HTC bottoms stream was never properly appreciated even in U.S. Pat. No. 4,614,643 to Doane, (co-inventor with Burks, Jr., filed much later than the '473 reference and also assigned to Stauffer), which suggests a tarry bottoms stream from a still can be treated with water and either filtered or centrifuged. More particularly, the '643 patent discloses mixing a wide variety of $FeCl_3$-containing chlorocarbon streams, treating them in an intermediate processing section in which the products are treated using any one or more "unit operation" steps, then distilling the treated stream in a still to recover valuable chlorocarbons. The bottoms stream from the still contained the $FeCl_3$ to be removed. Just enough water is added to this bottoms stream to convert the $FeCl_3$ to $FeCl_3.6H_2O$ (hexahydrate) which is then removed either by filtering or centrifuging the stream. The operability of the process depends upon the presence of the solid $FeCl_3.6H_2O$ which can be centrifuged because even the diluted waste stream is unflitrable.

The '643 patent acknowledges that German patent No. 2,540,292 states that an ordinary washing of EDC with water is not generally satisfactory for removing $FeCl_3$, therefore uses a multi-stage side channel pump. The '473 and '643 patents both refer to the teachings of Japanese Patent Publication No. 13606/1966 which discloses that dilute acid is preferred over water for washing a product EDC stream because of the emulsification problem (when using water). Note however, that product EDC, even if it is the bottoms from a LTC reactor, has much less than 100 ppm Fe; if the EDC is the overhead from the HTC column, or any other column in the process train, the EDC contains less than 10 ppm Fe, more typically less than 1 ppm.

In no instance does the EDC from any of the foregoing sources generate an emulsion when it is acidified with dilute HCl, irrespective of the acid concentration. Clearly there is nothing in the obvious treatment of a Fe-containing EDC stream with dilute HCl acid, to enable one to discover that within a particular range of elemental Fe concentration, a predominantly EDC bottoms stream containing at least 15% CHC heavies and tar, would generate such an intractable emulsification problem, nor that this problem could be solved if the emulsion was thoroughly mixed with at least a 50-fold excess of dil HCl in the 2%–4% range.

The numerous prior art references referred to in the '473 and '643 patents uniformly deal with an essentially EDC stream contaminated with an unspecified, and when specified, small amount of $FeCl_3$, not a concentration in the critical range of from 2000–4000 ppm Fe; nor do they deal with EDC contaminated with a large proportion of highboils and solids. None of the many prior art references suggests what we discovered, namely how disabling the emulsification problem really is with such a high Fe concentration in EDC containing at least 15% by wt CHC highboils and tarry solids.

It is evident that, if iron is precipitated as ferric hydroxide by distillation in a heavies column, the precipitated ferric hydroxide could not be removed from the feed to the Catoxid reactor, and the ferric hydroxide cannot be, because it would leave the bottoms of the heavies column with the heavies to be combusted. In an essentially EDC stream, contaminated with 1000 ppm $FeCl_3$ and less than 5 percent by wt highboils, neither adsorption nor distillation and subsequent filtration is an operating problem. As long as the concentration of $FeCl_3$ in the bottoms draw-off from the HTC reactor is outside the range of from 2000 ppm to 4000 ppm Fe, neither the physical and chemical structure of the highboils and tar, nor the amount in which they are formed are such that formation of the resulting emulsion is a critical debilitating factor.

A technical appreciation of just how intractable a problem results from treating chlorocarbons with an aqueous acid solution is detailed in U.S. Pat. Nos. 4,307,261 and 4,412,086 to Beard et al who state "The most obvious method of removing ferric chloride from chlorinated hydrocarbon streams is the extracton of the ferric chloride with aqueous acid solutions. The ferric chloride is unexpectedly difficult to remove in this manner. Part of the ferric chloride apparently retains some solubility in the organic layer by forming complexes with polymeric material. Furthermore, the resulting chlorinated hydrocarbon product must be dried, which is an expensive procedure on an industrial scale." (see the '261 patent, 1, lines 27–36; the '086 patent, col 1, lines 31–40). In other words, extracting ferric chloride from any CHC stream with dilute acid would be obvious if it were not for the emulsification problem. We agree, except that we do not "dry" the product to burn it in the Catoxid reactor.

Our invention avoids filtering the bottoms draw-off stream, except for gross tarry material which can be removed in a basket filter with a mesh size large enough to avoid being blinded, allows separation of the unfltrable acidified organic and aqueous phases by decantation because no emulsion is formed, and permits directly flowing a non-toxic, neutralized but slightly alkaline acidtreated organic phase to a heavies column for recovery of EDC, and permits the bottoms from the heavies column or a tar still to be incinerated in a Catoxid reactor, thus providing a simple and practical solution to a difficult problem.

SUMMARY OF THE INVENTION

It has been discovered that, under certain operating conditions, an emulsion of an acidified unfiltrable tarry bottoms stream from a HTC reactor can be demulsified and separated in a phase separation tank. A separated organic waste stream drawn from the lower layer of the phase separation tank, is found to consist essentially of at least 50%, preferably 60–70% by wt, of EDC, the remainder being chlorocarbons contaminated with no more than 5 ppm of Fe in it. The presence of $FeCl_3$ in an amount more than 5 ppm Fe in the separated organic waste, fouls the reboiler and lower internals of a "heavies" column in which the separated organic waste is concentrated, and deactivates the catalyst in a Catoxid fluid bed reactor in which the concentrate is burned.

It has further been discovered that by maintaining an iron salt chlorination catalyst in a concentration which results in 2000 ppm to 4000 ppm of Fe in the acidified HTC reactor bottoms, and operating the HTC reactor at a temperature in the range from about 90° C. to 120° C. and a pressure in the range from 9 psig to 12 psig, with from 3 to 5% by weight of ethylene in excess over the amount stoichiometrically required, an unfiltrable reactor bottoms drawoff is produced which may be acidified without forming an emulsion. Formation of an emulsion is avoided by mixing each volume of the HTC bottoms drawoff with at least 50 volumes of dilute aqueous HCl in a concentration range from 2 to 4% so as to produce an emulsion-free mixture of aqueous and organic phases. The mixture is gravity-separated in a phase separation tank by decantation. The upper layer is a waste water stream sent for further treatment before disposing of it, and the lower layer of heavies contains no more than than 5 ppm Fe. This lower layer is sent to a heavies column to be concentrated by recovering EDC overhead and producing a bottoms concentrate in which the Fe may be concentrated to no more than 50 ppm. The concentrate may be economically disposed of in a Catoxid reactor using a support-free gamma alumina catalyst found to be highly sensitive to iron.

More specifically, this invention is based on the discovery that, if the HTC reactor is operated as specified, taking a drawoff containing at least 60% by wt of EDC and 15% by wt heavies, and the concentration of iron salt catalyst maintained in the reactor to yield an acidified drawoff having a Fe concentration in the range from 2000–4000 ppm, then such organic complexes as are formed with solid, or semi-solid byproducts, polymeric chlorocarbons and the like, result in an emulsion which can be demulsified for gravity separation. When this combination of requirements is met, the emulsion is demulsified when the HTC reactor bottoms drawoff is mixed with a 50-fold, or more, excess of dilute aqueous hydrochloric acid wash having a concentration in the range from 2 to 4 percent by wt, computed as the weight of HCl per 100 parts of water.

It is therefore a specific object of this invention to utilize the foregoing discoveries to provide a simple, economical and efficient process in which the combined operations of a HTC reactor, a heavies column, and a Catoxid reactor may be continuously carried out without substantially fouling the internals of the heavies column, or deactivating the oxidation catalyst. Typically the heavies column can be operated without a shut-down for about six months, and the catalyst in the Catoxid reactor need not be replaced for at least a like period.

BRIEF DESCRIPTION OF THE DRAWING

The foregoing and other objects and advantages of this invention will appear more fully from the following description, made in connection with the accompanying drawing which schematically illustrate a preferred embodiment of the invention. The drawing is a simplified schematic flow diagram illustrating the relationship of a typical boiling reactor which is a particular embodiment of a high temperature chlorination (HTC) reactor, a phase separation tank with recycle, a recovery scheme for EDC in the separated organic waste, and a "Catoxid" fluid bed reactor. The bottoms stream drawoff from the HTC reactor is acidified, separated into two phases and disposed of without unacceptably posioning the catalyst in the Catoxid reactor.

DETAILED DESCRIPTION OF PREFERRED EMBODIMENTS

Since this invention is based on utilizing the discovery of how to demulsify an emulsion which is formed under particularly sepcified conditions, the invention is described particularly with respect to the operating relationship of the HTC reactor (which is a boiling reactor), and a fluid bed catalytic oxidation reactor in which the oxidation catalyst is a support-free gamma alumina catalyst. The alumina catalyst is adversely sensitive to ferric chloride, particularly if it ($FeCl_3$) is present in a concentration resulting in more than 50 ppm Fe in a waste organic stream to be oxidized in the reactor. It will be understood that the invention is equally applicable to any direct chlorination reactor in which the reaction of chlorine and ethylene is catalyzed by controlling the concentration of iron salt so that Fe is in the range from 2000 ppm to 4000 ppm, and which requires a bottoms draw-off to purge the reactor of an otherwise continuous increase of catalyst and highboils. Though the HTC reactor produces a substantially pure (99.+%) EDC effluent containing from about 100 ppm to about 0.5% by wt of chlorine, and relatively small amounts (relative to the volume of draw-off from the HTC reactor), of nitrogen, HCl, ethylene, oxygen and water vapor, a buildup of polychlorinated highboils in the liquid 1,2-dichloroethane reaction medium is unavoidable if not controlled by the bottoms draw-off.

Typically, the EDC effluent contains ethylene in the range from about 500 ppm to about 1.0%; polychlorinated compounds in the range from about 50 ppm to about 0.1%; HCl in the range from about 0.5% to about 7%; nitrogen in the range from about 0.4% to about 20%; and oxygen in the range from about 0.1% to about 5% by wt based on the combined components of the HTC effluent, along with small amounts of carbon dioxide and ethane.

Referring to the drawing in which pumps, overhead condensers, reboilers and other process equipment ancillary to the main units are not shown to keep the description simple, there is shown a schematic flow diagram of a HTC reactor indicated generally by reference numeral 10, in which liquid EDC containing $FeCl_3$ or other ferric salt in a concentration sufficient to provide the aforespecified concentration of Fe, is held under elevated pressure, preferably from about 9 psig to about 15 psig, at its boiling point. A slight molar excess of ethylene, from about 1% to about 5% over the stoichiometric amount necessary to react with chlorine and form EDC, referred to herein as "excess ethylene", is fed through an ethylene feed line 11, and chlorine is fed through a chlorine feed line 12, both near the bottom, so that they react exothermically within hot liquid chlorinated hydrocarbons (chlorohydrocarbon or chlorocarbon "CHC" liquid), mainly EDC, held as the liquid reaction medium in the reactor.

The liquid CHC normally includes minor amounts of 1,1,2-trichloroethane ("triane"), 1,1,1- or 1,1,2,2-tetrachloroethane, and pentachloroethane, and other CHC impurities formed in the HTC reactor due to side reactions.

The heat of reaction boils off EDC while the reaction is controlled so that the reaction mass is maintained at a temperature of about 115° C. in the range of pressure stated hereinabove.

In a typical commercial facility, there is also provided a low temperature chlorination (LTC) reactor 15, operating below the boiling point of EDC, but in which reactor 15 there is also carried out the catalytic chlorination of ethylene in a liquid medium. The chlorine and ethylene are introduced through lines 16 and 17 respectively, and the reaction mass is depleted by withdrawing a LTC bottoms stream 18 which is remarkably free from semisolids and emulsifiers, and is therefore introduced into the suction of pump 32, to provide additional organic phase to help break the emulsion formed by the HTC bottoms. The LTC bottoms stream 18, by itself, may be acidifed with dilute aqueous HCl in essentially any concentration, and in any amount, provided the amount is large enough to react with and dissolve all the ferric salt in the stream, then easily separated by decantation because there is not enough, if any, emulsion formed to interfere with the separation.

The chlorine is deliberately "doctored" with oxygen present in the range from about 0.1% to about 1% by wt of the combined flow of ethylene, chlorine and oxygen, to increase the selectivity to EDC, and to inhibit the free radical reactions which produce triane and other polychlorinated highboils having more than two Cl atoms in each molecule. The rate of withdrawal of HTC reactor bottoms draw-off 13 is such as to maintain a deliberately high concentration of at least 15% by weight liquid highboils (CHC which do not boil at the operating temperature and pressure of the HTC reactor), and semi-solid tar which latter would not be fluent at the HTC operating conditions if the tar was not suspended or dissolved in the EDC. Such semi-solid tarry material, free of EDC, characteristically can be spooned into a mound onto a flat surface and the mound retains its overall shape at room temperature. Since a concentration of 2000 ppm to 4000 ppm Fe is to be maintained in the reaction medium in the HTC, this is the concentration of Fe in the draw-off.

The oxygen is conveniently introduced by injecting air into either the chlorine feed line, or into a separate sparger. This injection of air introduces a relatively large amount of nitrogen, comparable in volume to the amount of excess ethylene present in the effluent, which nitrogen simply "rides through" the system. The presence of this oxygen, though beneficial for the reaction producing EDC, also produces an unavoidably large amount of highboils boiling in the range above 130° C., including semi-solids which of course cannot be boiled off.

The chlorine feed, whether liquid or gas, is not dry, for one reason or the other. Typically the moisture is present because the chlorine is derived from electrolytic cells. The level of moisture varies, ranging from about 20 parts per million (ppm) to about 1% by wt of the chlorine, more likely in the range from about 50 ppm to about 300 ppm. In addition to this water coming into the reactor with the chlorine, a lesser amount in the range from 1 ppm to about 50 ppm may come in with the ethylene, depending upon its source. Further, a small amount of water may be generated by side reactions in the reactor. All the water introduced is distributed, when it leaves the reactor, between the overhead effluent leaving the reactor near its top, through line 14, and the bottoms line 13. The concentration of water in the bottoms draw-off is in the range from about 0 ppm to about 10 ppm. Though the concentration of water is of no particular importance for the purpose of treating the bottoms stream prior to incinerating it, the concentration of water provides an excellent indication of the operating characteristics of the HTC reactor.

The effluent in line 14 is led into a product column 20, near its bottom and the overhead from the column is product EDC, at least 98% pure, which leaves the product column through line 23 and is recovered in a conventional manner, for example, as described in copending U. S. application Ser. No. 908,744 to Cowfer, the disclosure of which is incorporated by reference thereto as if fully set forth herein. The product column is a distillation column fitted with trays or other conventional vapor-liquid equilibria staging means, and a portion of the bottoms from the product column is recycled through recycle line 21 to the HTC reactor. This recycle from the product column is only of interest in this invention because the recycle tends to increase the concentration of highboils and tar in the bottoms draw-off from the HTC reactor. The bottoms from the product column is led through line 22 to further purification for recovery of specific chlorocarbons, or, if desired, may be led into the heavies column 70 or tar still 80 to recover additional EDC.

The bottoms stream 13 a mixture of organic and aqueous phases which is flowed through a basket filter 30 to remove agglomerates larger than about 10 mesh (2 mm), so that the semi-solid tar is present as a fine suspension in the predominantly EDC stream contaminated with from about 15% to as much as 40% by weight of highboils, flowing through line 31. It is this stream, with its high concentration of Fe and the presence of liquid and semisolid emulsifiers which forms the emulsion which, until this invention, succesfully defied being broken.

This stream 31 is pumped by pump 32 through line 33 to phase separation drum 40. The phase separation drum is sized so as to provide a residence time of no more than 30 min, preferably less than 15 min, during which time the mixed phases separate into an upper aqueous layer and a lower organic layer. A longer residence time is of no benefit if an emulsion forms, and, it will be evident that, efficiency demands as short a residence time as is practical. The short residence time is an indication of how effectively the emulsion is broken up.

The upper layer is withdrawn as a recycle stream through line 43 into which HCl acid is flowed through line 42. The concentration and amount of HCl acid flowed is controlled so that the concentration of HCl acid in the aqueous phase in line 43 is in the range from 2% to 4% by weight. Make-up water is added through line 46 in about the same amount as the bottoms draw-off from the HTC, namely about 5 gpm (gals per min) to about 15 gpm, this amount also being sufficient to replace the volume of waste water withdrawn from the upper aqueous acid phase in the drum, and sent to waste water treatment. It is a particular advantage that the volume of make-up water is no more than that of the HTC bottoms withdrawn because the low make-up permits the concentration of dilute HCl in the recycle to be maintained within the specified limits more easily.

To demulsify the emulsion being flowed into the drum 40, and obtain the separation of the phases in the desired amount of time, the flow ratio of the acidified aqueous recycle stream in line 43 to the flow of HTC bottoms in line 31 is at least 50, and preferably in the range from 75 to 150. It is obvious that, since less than 1 gpm of aqueous acid will be more than enough to dissolve the 2000–4000 ppm of Fe in the HTC bottoms stream which is less than 20 gpm, this (recycle) : (HTC bottoms) ratio is very large in relation to the amount of Fe salt to be extracted into aqueous solution. But the high ratio is necessary to break the emulsion. When this ratio is maintained in the specified range, and the concentration of HCl is maintained in the 2%–4% range, the mixed recycle and bottoms streams in lines 31 and 43 separate into aqueous acid and organic phases within the specified residence time.

The lower layer of CHC from the drum 40 is the separated waste organic stream led through line 45 to a caustic wash drum 50 into which is also introduced EDC through line 52 from an oxychlorination ("oxy") reactor in another part of the plant. The combined streams in 45 and 52 are contacted with enough alkali flowing through line 51 to neutralize the HCl acid. It is preferred to use a slight excess of alkali, typically aqueous sodium hydroxide. The slightly alkaline stream flowing through line 53 now contains no more than 10 ppm, and preferably less than 5 ppm Fe, and is pumped directly to a concentration zone in a recovery train including plural separation zones, the first of which is a light ends column 60, where components boiling lower than EDC, along with traces of alkaline water are taken overhead through line 61.

The bottoms from the light ends column 60 are flowed through line 62 to heavies column 70 in which EDC, at least 98% pure, is taken overhead through line 71. The bottoms from the heavies column is flowed through line 72 to tar still 80, where again, an overhead which is at least 98% EDC is taken through line 81. The effect of stripping valuable EDC from the stream 53 is to concentrate the Fe in the bottoms stream 82 from the tar still. It is in this stream 82 that the level of Fe is to be kept at 50 ppm, or lower, before it is flowed to the Catoxid reactor 90, or the gamma alumina catalyst in the reactor is poisoned. The feed to the Catoxid reactor consists essentially of a major proportion by wt of CHC heavies and a minor proportion of EDC. The reactor is operated under pressure in the range from about 50 psig to about 100 psig, and a temperature in the range from about 450° F. to about 550° F. with an excess of air. Air is flowed through line 91 into the reactor 90, near its bottom to fluidize the catalyst and oxidize the waste CHC in stream 54. The vent from the Catoxid reactor is led through line 92 for further treatment before disposing of it.

It is particularly noteworthy that, it is only the peculiar characteristic of the unsupported gamma alumina catalyst, namely its deactivation or adverse sensitivity to ferric chloride, that makes this process necessary. Several oxidation catalysts supported on an inert support are far less sensitive to poisoning by metals, particularly Fe, but have other drawbacks, mainly less efficient oxidation of the highboils and semi-solids. The cost of replacement of the gamma alumina catalyst is of paramount economic importance. Therefore, the ability to operate a plant which produces about 600 million pounds per year of EDC without replacing the gamma alumina for periods exceeding six months, is of particular commercial significance.

The following example illustrates the process as it is carried out in a commercial EDC plant with the flow rates specified herebelow:
Ethylene to HTC: 20,000–25,000 lb/hr
Chlorine to HTC: 60,000–65,000 lb/hr
Anhydrous HCl to maintain specified concentration: 1000–2000 ft$^3$/hr
Recycle from product column to HTC: 900–1000 gpm
HTC reactor bottoms draw-off: 8–12 gpm
Make-up water: 8–12 gpm
Mixed phases to separation drum: 1100–1200 gpm
Recycle from upper layer of separation drum: 1000–1100 gpm
Residence time in separation drum: less than 30 min.
Waste water from upper layer of separation drum: 8–12 gpm
Separated organic waste from lower layer: 60–70 gpm
Caustic flow to produce slightly alkaline feed to light ends column: 5–10 gpm of 5% NaOH
Feed to Catoxid reactor: 500–1000 lb/hr
If added, EDC from LTC: 150–250 gpm
Catalyst not deactivated after six months.

In each of the examples hereinbelow, 10 gpm of bottoms draw-off from a HTC reactor operating within the parameters set forth hereinabove is filtered through a basket filter fitted with a 10 mesh (2 mm) screen to remove very large solids and agglomerates, before the draw-off is treated further, unless specified otherwise.

EXAMPLE 1

A. The bottoms draw-off, without being acidified, is filtered through a 18"×18" filter press fitted with 80 mesh screen. The 80 mesh screen is blinded within 1 hr.

B. The bottoms draw-off is acidified with a 10-fold volume of 3% dilute HCl acid and filtered through the filter press fitted with 80 mesh screen. The 80 mesh screen is again blinded within 1 hr.

EXAMPLE 2

A. The bottoms draw-off is thoroughly mixed with 100 volumes of 3% dil HCl and allowed to settle by gravity. The aqueous and organic phases separate within 30 min.

B. The bottoms draw-off is thoroughly mixed with 10 volumes of 3% dil HCl and allowed to settle by gravity. The aqueous and organic phases do not separate within 24 hr.

C. The bottoms draw-off is thoroughly mixed with (a) 160 gpm of product EDC from a LTC reactor operating as described hereinbefore, the EDC containing about 20 ppm Fe present as $FeCl_3$, and (b) 900 gpm of 3% dil HCl and allowed to settle by gravity. The aqueous and organic phases separate within 30 min.

D. The bottoms draw-off is thoroughly mixed with (a) 160 gpm of product EDC from a LTC reactor operating as described hereinbefore, the EDC containing about 20 ppm Fe present as $FeCl_3$, (b) 10 gpm of combined heavies CHC streams together containing about 100-200 ppm of Fe present as $FeCl_3$, and (c) 900 gpm of 3% dil HCl, and allowed to settle by gravity. The aqueous and organic phases do not separate after 24 hr.

EXAMPLE 3

A. The bottoms draw-off is thoroughly mixed with 960 gpm of 1% dil HCl and allowed to settle by gravity. The aqueous and organic phases do not separate within 24 hr.

B. The bottoms draw-off (filtered through the basket filter) is then filtered through the 18"×18" filter press freshly fitted with 80 mesh screen. Before the screen is blinded, a sample of filtrate is obtained which is thoroughly mixed with 3 volumes of 1.0N aqueous HCl for 2 min, and allowed to settle by gravity. The aqueous and organic phases do not separate within 24 hr.

C. A portion of the filtrate obtained before the 80 mesh screen is blinded is filtered through a 325 mesh screen (44 microns). The 325 mesh screen is blinded within 1 hr.

D. A portion of the filtrate obtained before the 80 mesh screen is blinded is thoroughly mixed with 3 volumes of 3% aqueous dil HCl for 2 min, and allowed to settle by gravity. The aqueous and organic phases do not separate within 24 hr.

We claim:

1. A continuous process for detoxifying a waste chlorocarbon stream to be contacted with an oxidation catalyst adversely sensitive to the presence of iron, comprising, (a) contacting ethylene with chlorine in predominantly liquid 1,2-dichloroethane in the presence of sufficient iron-containing chlorination catalyst to provide from 2000 ppm to 4000 ppm of iron, as elemental Fe, at a temperature in the range from 90° C. to 120° C. and superatmospheric pressure below 25 psig in a chlorination reactor, (b) withdrawing a bottoms draw-off from said chlorination reactor, said bottoms draw-off containing said concentration of Fe and consisting essentially of at least 60% by weight of 1,2-dichloroethane, at least 15% by weight of liquid chlorocarbon highboils, including a semi-solid tar, having a higher boiling point than 1,2-dichloroethane, (c) mixing each volume of said bottoms draw-off with at least fifty volumes of dilute aqueous hydrochloric acid having a concentration in the range from 2% to 4% by weight, so as to form a mixed two-phase unfiltrable stream of an aqueous acid phase containing ferric chloride, and an organic phase containing said highboils, (d) flowing said unfiltrable two-phase stream, without separating any solids therein, into a quiescent zone to provide a residence time of less than 0.5 hr, within which time aqueous acid and organic phases are separated in the upper and lower portions of said quiescent zone, (e) withdrawing a separated waste organic stream from the lower portion of said quiescent zone, said separated waste organic stream containing less than 5 ppm Fe, (f) contacting said separated waste organic stream with sufficient alkali to provide an alkaline separated waste organic stream in which said ferric chloride is converted to ferric hydroxide, (g) directly flowing said alkaline separated waste organic stream, without separating any solids therein, into a concentration zone for recovery of said 1,2-dichloroethane, (h) removing substantially pure 1,2-dichloroethane from the overhead of said concentration zone, and a heavies concentrate from the bottoms of said concentration zone, (i) flowing said heavies concentrate, without separating any solids therein, to an oxidation zone containing a fluid bed of gamma alumina catalyst, said oxidation zone being maintained at a temperature and pressure sufficient to oxidize said alkaline separated waste organic stream and convert it mainly to hydrochloric acid, carbon dioxide, carbon monoxide and water, and, (j) operating said oxidation zone continuously with essentially no loss of catalytic activity.

2. The process of claim 1 wherein said withdrawing of bottoms from the chlorination reactor is at a rate of about 5 gpm to about 15 gpm.

3. The process of claim 2 wherein said concentration zone includes a light ends separation zone, a heavies separation zone and a tar separation zone, and said elemental Fe content of said alkaline separated waste organic stream is concentrated in the bottoms of said tar separation zone to a level below 50 ppm.

4. The process of claim 3 wherein said mixed two-phase unfiltrable stream includes the flow of product EDC produced in a low temperature chlorination reactor operating at a temperature in the range from about 50° C. to about 65° C., and no other chlorocarbon stream containing ferric salts.

* * * * *